(12) United States Patent
Kato

(10) Patent No.: US 6,743,176 B2
(45) Date of Patent: Jun. 1, 2004

(54) ULTRASONIC IMAGE DISPLAY APPARATUS AND ULTRASONIC IMAGE DISPLAY METHOD

(75) Inventor: Sei Kato, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/417,482

(22) Filed: Apr. 17, 2003

(65) Prior Publication Data

US 2003/0199766 A1 Oct. 23, 2003

(30) Foreign Application Priority Data

Apr. 18, 2002 (JP) ........................................ 2002-115973

(51) Int. Cl.[7] .................................................. A61B 8/00
(52) U.S. Cl. .................................................... 600/440
(58) Field of Search ........................ 600/437, 440–441, 600/443, 447; 382/132

(56) References Cited

U.S. PATENT DOCUMENTS

| | | | | |
|---|---|---|---|---|
| 4,773,425 A | * | 9/1988 | Saitou | 600/440 |
| 4,787,393 A | * | 11/1988 | Fukukita et al. | 600/440 |
| 5,182,728 A | * | 1/1993 | Shen et al. | 367/7 |
| 5,250,933 A | | 10/1993 | Beaudin et al. | |
| 5,274,759 A | | 12/1993 | Yoshioka | |
| 5,367,318 A | | 11/1994 | Beaudin et al. | |
| 5,740,267 A | * | 4/1998 | Echerer et al. | 382/132 |
| 5,840,034 A | | 11/1998 | Amemiya et al. | |
| 6,084,565 A | * | 7/2000 | Kiya | 345/115 |
| 6,139,497 A | | 10/2000 | Amemiya et al. | |
| 6,217,515 B1 | | 4/2001 | Yamakawa et al. | |

* cited by examiner

*Primary Examiner*—Francis J. Jaworski
(74) *Attorney, Agent, or Firm*—Carl B. Horton, Esq.; Armstrong Teasdale LLP

(57) ABSTRACT

For the purpose of improving monitor display condition operating ease and enabling easy display of an arbitrary site, an ultrasonic image based on an echo signal received by an ultrasonic probe 3 is produced by an image producing section 12, a display area is formed on a screen by a display area forming section 17, a displayed range of the ultrasonic image to be displayed in the display area is selected by a displayed range selecting section 14, and scrolling of a selected range and rotation of the displayed range are achieved by a displayed range moving section 15 and a displayed range rotating section 16, respectively, based on a position on the monitor screen specified by the pointing device 3.

20 Claims, 13 Drawing Sheets

ULTRASONIC IMAGE DISPLAY APPARATUS AND ULTRASONIC IMAGE DISPLAY METHOD

This application claims the benefit of Japanese Application No. 2002-115973 filed Apr. 18, 2002.

BACKGROUND OF THE INVENTION

The present invention relates to an ultrasonic image display apparatus and ultrasonic image display method for producing an ultrasonic image based on an echo signal output by an ultrasonic probe and displaying the ultrasonic image on a monitor, and more particularly to an ultrasonic image apparatus and ultrasonic image display method that improve monitor display condition operating ease and enable easy display of an arbitrary site.

Conventionally, an ultrasonic image display apparatus for imaging the interior of a subject by applying ultrasound to a region to be examined in the subject with an abutting ultrasonic probe, and producing an image of an echo signal of reflected waves of the applied ultrasound is commonly used in non-destructive examination. Since ultrasound is harmless to a living body, the ultrasonic image display apparatus is especially useful for medical applications and is used for detection of foreign material in the living body, determination of lesion degree, observation of a tumor or a fetus, and the like.

In the conventional ultrasonic image display apparatus, in general, a display method of displaying a single ultrasonic image produced based on an echo signal and a display method of simultaneously displaying a plurality of ultrasonic images are switchably used. The method of displaying a single ultrasonic image is used for displaying the whole ultrasonic image produced from an echo signal on a monitor, and the method of simultaneously displaying a plurality of ultrasonic images is used for comparison between the ultrasonic images. When the plurality of ultrasonic images are displayed, the screen of the monitor must be allocated among a plurality of display areas, and accordingly the display area available for displaying each ultrasonic image becomes smaller. To display the ultrasonic images in sufficient resolution and size, part of each ultrasonic image produced from an echo signal must be selectively displayed. Therefore, the ultrasonic image display apparatus selectively displays necessary parts of ultrasonic images for comparison between the ultrasonic images by switching the display between the single ultrasonic image display and multiple ultrasonic image display.

Moreover, the ultrasonic image display apparatus usually has a function of measuring distance, area, volume, and the like in the ultrasonic image. In measuring distance in the ultrasonic image, a pointing device capable of specifying an arbitrary point on the monitor, such as a mouse, is employed and two arbitrary points are specified to calculate the distance therebetween; or an arbitrary curve is specified using the pointing device to calculate the length thereof. In measuring an area, an arbitrary region is specified using the pointing device to calculate the area of that region. In measuring volume, processing for calculating the volume from area and distance measurements is executed. When distance, area or volume is to be calculated as described above, the single display by which the whole ultrasonic image can be displayed is more suitable than the multiple display by which only part of the ultrasonic image is displayed, because the locations to be specified must be displayed on the monitor.

Furthermore, when an echo signal received by the ultrasonic probe is displayed as an ultrasonic image, the operator must hold the ultrasonic probe against the region to be examined and operate the ultrasonic image display apparatus at the same time. Usually, the ultrasonic image display apparatus must be operated by one hand because the other hand is used for holding the ultrasonic probe. Therefore, ease of operation in operating the ultrasonic image apparatus is very important. For example, it is desirable that the operation for switching between the single display and multiple display described above can be easily done by one hand, and that a desired portion of the ultrasonic image can be displayed.

In the conventional ultrasonic image display apparatus described above, when part of an ultrasonic image is displayed in the multiple display and a certain location of the ultrasonic image not in that part is to be displayed, the multiple display must be switched to the single display. Therefore, when measurement of distance or area is to be made on locations including those not displayed in the multiple display, processing for switching from the multiple display to the single display is required, thus imposing limitation on the measurement in the multiple display. That is, the conventional ultrasonic image display apparatus requires the operator to conduct cumbersome operations, leading to problems that ease of operation is reduced and the time needed for the operations is increased.

SUMMARY OF THE INVENTION

Therefore, an object of the present invention is to provide an ultrasonic image display apparatus and ultrasonic image display method that improve monitor display condition operating ease and enable easy display of an arbitrary site.

To solve the aforementioned problems and attain the object, the present invention in accordance with a first aspect provides an ultrasonic image display apparatus for producing an ultrasonic image based on an echo signal received by an ultrasonic probe and displaying said ultrasonic image on a monitor, said apparatus characterized in comprising: display area forming means for forming on a screen of said monitor a display area in which at least part of said ultrasonic image is displayed; displayed range selecting means for selecting a displayed range to be displayed in said display area from said ultrasonic image; displayed range moving means for conducting movement of said displayed range of said ultrasonic image; and movement instruction inputting means for inputting a direction and an amount of the movement of said displayed range to said displayed range moving means.

According to the invention of the first aspect, the ultrasonic image display apparatus produces an ultrasonic image based on an echo signal received by an ultrasonic probe, forms a display area for displaying the ultrasonic image on a monitor screen, selects a displayed range to be displayed in the display area from the ultrasonic image, and allows scrolling of the displayed range of the ultrasonic image.

The present invention in accordance with a second aspect is, in the invention in accordance with the first aspect, characterized in that said ultrasonic image display apparatus further comprises position specifying means for specifying an arbitrary position on said monitor screen, and when the position specified by said position specifying means is moved from the inside to the outside of said display area, said displayed range moving means conducts movement of said displayed range according to the amount of said movement.

According to the invention of the second aspect, when an arbitrary position on the monitor screen specified by the position specifying means is moved from the inside to the outside of the display area, the ultrasonic image display apparatus scrolls the displayed range according to the amount of the movement.

The present invention in accordance with a third aspect is, in the invention in accordance with the second aspect, characterized in comprising a single user interface that operates as said movement instruction inputting means or said position specifying means by switching its operation.

According to the invention of the third aspect, the scrolling of the displayed range can be conducted in a plurality of methods by switchably using a single user interface.

The present invention in accordance with a fourth aspect is, in the invention in accordance with any one of the first–third aspects, characterized in that said display area forming means is capable of switching display between single display in which a single display area is formed on said monitor screen and multiple display in which a plurality of display areas are formed on said monitor screen.

According to the invention of the fourth aspect, the ultrasonic image display apparatus is capable of switching display between single display in which a single display area is displayed on the monitor screen and multiple display in which a plurality of display areas are displayed, and allows scrolling of the displayed range of an ultrasonic image in the single or multiple display.

The present invention in accordance with a fifth aspect is, in the invention in accordance with any one of the first–fourth aspects, characterized in that said ultrasonic image display apparatus further comprises image storing means for storing an ultrasonic image converted from said echo signal as still image data, and said displayed range selecting means selects an ultrasonic image to be displayed and its displayed range from among said ultrasonic image converted from said echo signal and ultrasonic images stored in said image storing means.

According to the invention of the fifth aspect, the ultrasonic image display apparatus can arbitrarily select an ultrasonic image to be displayed in a display area from among a scan image produced from an echo signal and ultrasonic images stored in the image storing means, and allows scrolling of the displayed range.

The present invention in accordance with a sixth aspect is, in the invention in accordance with any one of the first–fifth aspects, characterized in that when said display area forming means forms a plurality of display areas, said displayed range selecting means selects ultrasonic images to be displayed and their displayed ranges respectively for said plurality of display areas.

According to the sixth aspect, when a plurality of display areas are displayed on the monitor screen, the ultrasonic image display apparatus can arbitrarily select ultrasonic images to be displayed in respective display areas from among a scan image produced from an echo signal and ultrasonic images stored in the image storing means, and allows scrolling of the displayed ranges.

The present invention in accordance with a seventh aspect is, in the invention in accordance with any one of the fourth–sixth aspects, characterized in that when said display area forming means switches display from the single display to the multiple display, said displayed range selecting means selects part of the ultrasonic image displayed in the single display as said displayed range, and displays said displayed range in at least one of said plurality of display areas.

According to the invention of the seventh aspect, when display is switched from the single display to the multiple display, the ultrasonic image display apparatus selects part of the ultrasonic image displayed in the single display as the displayed range, and displays it in at least one of the plurality of display areas.

The present invention in accordance with an eighth aspect is, in the invention in accordance with any one of the first–seventh aspects, characterized in further comprising displayed range rotating means for rotating said displayed range of said ultrasonic image.

According to the invention of the eighth aspect, the ultrasonic image display apparatus can rotate the displayed range of an ultrasonic image displayed in a display area to display the range at a desired angle.

The present invention in accordance with a ninth aspect provides an ultrasonic image display method for producing an ultrasonic image based on an echo signal received by an ultrasonic probe and displaying said ultrasonic image on a monitor, said method characterized in comprising: a display area forming step of forming on a screen of said monitor a display area in which at least part of said ultrasonic image is displayed; a displayed range selecting step of selecting a displayed range to be displayed in said display area from said ultrasonic image; a displayed range moving step of conducting movement of said displayed range of said ultrasonic image; and a movement instructing step of inputting a direction and an amount of the movement of said displayed range to said displayed range moving means.

According to the invention of the ninth aspect, the ultrasonic image display method produces an ultrasonic image based on an echo signal received by an ultrasonic probe, forms a display area for displaying the ultrasonic image on a monitor screen, selects a displayed range to be displayed in the display area from the ultrasonic image, and allows scrolling of the displayed range of the ultrasonic image.

The present invention in accordance with a tenth aspect is, in the invention in accordance with the ninth aspect, characterized in that said ultrasonic image display method further comprises a position specifying step of specifying an arbitrary position on said monitor screen, and when the position specified by said position specifying step is moved from the inside to the outside of said display area, said displayed range moving step conducts movement of said displayed range according to the amount of said movement.

According to the invention of the tenth aspect, when an arbitrary position on the monitor screen specified by the position specifying means is moved from the inside to the outside of the display area, the ultrasonic image display method scrolls the displayed range according to the amount of the movement.

The present invention in accordance with an eleventh aspect is, in the invention in accordance with the ninth or tenth aspect, characterized in that said movement instructing step and said position specifying step are executed by a single user interface.

According to the invention of the eleventh aspect, the scrolling of the displayed range can be conducted in a plurality of methods by switchably using a single user interface.

The present invention in accordance with a twelfth aspect is, in the invention in accordance with the ninth–eleventh aspect, characterized in that said display area forming step is capable of switching display between single display in which a single display area is formed on said monitor screen and multiple display in which a plurality of display areas are formed on said monitor screen.

According to the invention of the twelfth aspect, the ultrasonic image display method is capable of switching display between single display in which a single display area is displayed on the monitor screen and multiple display in which a plurality of display areas are displayed, and allows scrolling of the displayed range of an ultrasonic image in the single or multiple display.

The present invention in accordance with a thirteenth aspect is, in the invention in accordance with any one of the ninth–twelfth aspects, characterized in that said ultrasonic image display method further comprises an image storing step of storing an ultrasonic image produced based on said echo signal as still image data, and said displayed range selecting step selects an ultrasonic image to be displayed and its displayed range from among said ultrasonic image converted from said echo signal and ultrasonic images stored by said image storing step.

According to the invention of the thirteenth aspect, the ultrasonic image display method can arbitrarily select an ultrasonic image to be displayed in a display area from among a scan image produced from an echo signal and ultrasonic images stored in the image storing means, and allows scrolling of the displayed range.

The present invention in accordance with a fourteenth aspect is, in the invention in accordance with any one of the ninth–thirteenth aspects, characterized in that when said display area forming step forms a plurality of display areas, said displayed range selecting step selects ultrasonic images to be displayed and their displayed ranges respectively for said plurality of display areas.

According to the fourteenth aspect, when a plurality of display areas are displayed on the monitor screen, the ultrasonic image display method can arbitrarily select ultrasonic images to be displayed in respective display areas from among a scan image produced from an echo signal and ultrasonic images stored in the image storing means, and allows scrolling of the displayed ranges.

The present invention in accordance with a fifteenth aspect is, in the invention in accordance with the twelfth––fourteenth aspect, characterized in that when said display area forming step switches display from the single display to the multiple display, said displayed range selecting step selects part of the ultrasonic image displayed in the single display as said displayed range, and displays said displayed range in at least one of said plurality of display areas.

According to the invention of the fifteenth aspect, when display is switched from the single display to the multiple display, the ultrasonic image display method selects part of the ultrasonic image displayed in the single display as the displayed range, and displays it in at least one of the plurality of display areas.

The present invention in accordance with a sixteenth aspect is, in the invention in accordance with any one of the ninth–fifteenth aspects, characterized in further comprising a displayed range rotating step of rotating said displayed range of said ultrasonic image.

According to the invention of the sixteenth aspect, the ultrasonic image display method can rotate the displayed range of an ultrasonic image displayed in a display area to display the range at a desired angle.

Therefore, in the ultrasonic image display apparatus and ultrasonic image display method in accordance with the present invention for displaying an ultrasonic image produced based on an echo signal output by an ultrasonic probe in one or more display areas formed on the monitor screen, a displayed range of the ultrasonic image displayed in the display area can be scrolled in the display area; and therefore, an effect that there are provided an ultrasonic image display apparatus and ultrasonic image display method that improve monitor display condition operating ease and enable easy display of an arbitrary site is obtained.

Further objects and advantages of the present invention will be apparent from the following description of the preferred embodiments of the invention as illustrated in the accompanying drawings.

DETAILED DESCRIPTION OF THE INVENTION

An ultrasonic image display apparatus in accordance with an embodiment of the present invention will now be described in detail with reference to the accompanying drawings.

In this embodiment, an ultrasonic image display apparatus that allows use of a whole ultrasonic image in a limited display area by scrolling and rotating a portion of the ultrasonic image that is displayed on a monitor will be described.

Figure 1:
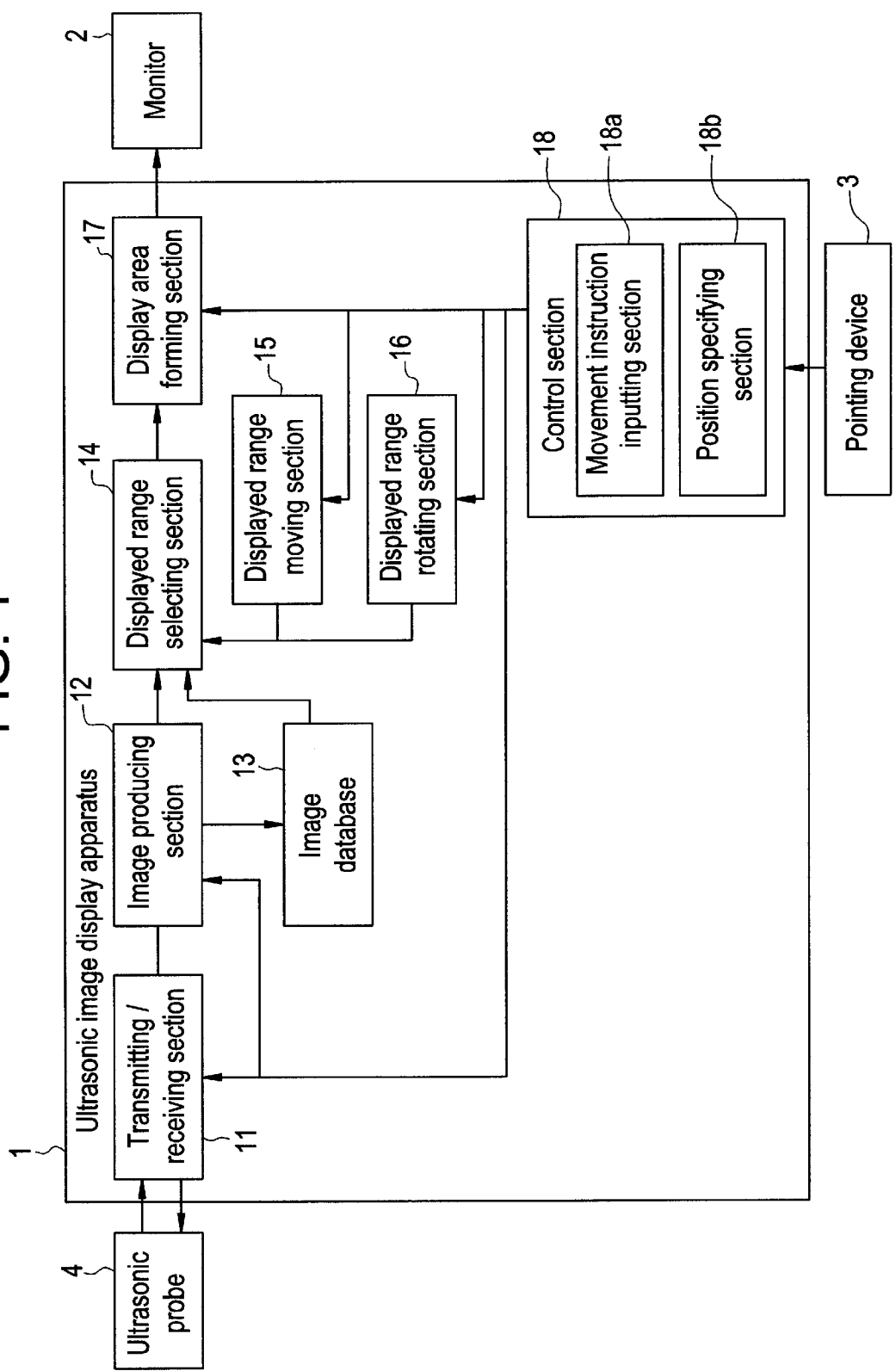
FIG. 1 is an explanatory diagram for explaining the overall configuration of an ultrasonic image display apparatus in accordance with the present embodiment.

FIG. 1 is an explanatory diagram for explaining the overall configuration of the ultrasonic image display apparatus in accordance with the present embodiment. In FIG. 1, the ultrasonic image display apparatus 1 is connected with a monitor 2, a pointing device 3, and an ultrasonic probe 4. The monitor 2 employed may be of any type, such as a CRT monitor or a liquid crystal monitor. The pointing device 3 is implemented by means for specifying arbitrary points on a screen of the monitor 2, such as a mouse, trackball, cursor key or the like.

The ultrasonic image display apparatus 1 comprises therein a transmitting/receiving section 11 connected to the ultrasonic probe 4, an image producing section 12 for producing an ultrasonic image from an echo signal received by the ultrasonic probe 4, an image database 13 for storing images produced by the image producing section 12, a display area forming section 17 for forming on the monitor 2 screen a display area in which the ultrasonic image is displayed, a displayed range selecting section 14 for determining a range of the ultrasonic image that is to be displayed in the display area, a displayed range moving section 15 for scrolling the displayed range of the ultrasonic image, a displayed range rotating section 16 for rotating the displayed range of the ultrasonic image, and a control section 18 connected with the pointing device 3 and an input interface which is not shown.

The control section 18 comprises therein a movement instruction inputting section 18a and a position specifying section 18b. The movement instruction inputting section 18a outputs to the displayed range moving section 15 a direction and an amount of movement supplied by the pointing device 3 as a direction and amount of movement of the displayed range of the ultrasonic image. The position specifying section 18b translates positional information supplied by the pointing device 3 into a position on the monitor 2 screen, and also translates movement of the pointing device 3 into movement on the screen. The control section 18 handles a plurality of types of processing in response to inputs from the pointing device 3 by switchably using the movement instruction inputting section 18a and position specifying section 18b.

The control section 18 also supplies a driving signal to the ultrasonic probe 4 via the transmitting/receiving section 11 to transmit ultrasound. The ultrasonic probe 4 receives an echo signal of reflected waves of the transmitted ultrasound and outputs the echo signal to the image producing section 12 via the transmitting/receiving section 11.

When an ultrasonic image is to be displayed using the ultrasonic image display apparatus 1, the ultrasonic probe 4 is first abutted against a region to be examined in a subject to transmit ultrasound, and the ultrasonic probe 4 receives an echo signal of reflected waves of the transmitted ultrasound. The image producing section 12 produces a scan image representing the echo signal received by the ultrasonic probe 4 as an image in real time. Thus, if a change in the echo signal received by the ultrasonic probe 4 arises, the ultrasonic image produced by the image producing section 12 varies according to the change. The control section 18 transmits a control command for directing the image producing section 12 to store the ultrasonic image when save of the ultrasonic image is commanded using the pointing device 3 or a console panel (not shown). When the control command to store the ultrasonic image is received from the control section 18, the image producing section 12 stores the ultrasonic image that is a scan image at that time in the image database 13.

The display area forming section 17 forms at least one display area in which the ultrasonic image is displayed on the monitor 2 screen. The displayed areas are defined by specifying the number of display areas, their sizes, and their locations. The displayed range selecting section 14 identifies an ultrasonic image to be displayed in a display area formed by the display area forming section 17, and its displayed range to be displayed in the display area. When a plurality of display areas are formed, the displayed range selecting section 14 selects ultrasonic images to be displayed and their displayed ranges for the respective display areas. Moreover, the displayed range selecting section 14 can arbitrarily select an ultrasonic image to be displayed in the display area from among the scan image produced by the image producing section 14 and the ultrasonic images stored in the image database 13.

The monitor 2 displays the ultrasonic image and its displayed range selected by the displayed range selecting section 14 in the display area formed by the display area forming section 17. By thus forming the display area by the display area forming section 17 and determining an ultrasonic image to be displayed in the display area and its displayed range by the displayed range selecting section 14, an arbitrary ultrasonic image can be selected and displayed to have a desired size, and ultrasonic image single display and multiple display can be switched.

Furthermore, the control section 18 modifies the displayed range using the movement instruction inputting section 18a or position specifying section 18b in response to an input from the pointing device 3. Specifically, when scrolling of the displayed range of the ultrasonic image is specified, a control command to move the displayed range is output to the displayed range moving section 15. When rotation of the displayed range of the ultrasonic image is specified, a control command to rotate the displayed range is output to the displayed range rotating section 16.

The displayed range moving section 15 scrolls the displayed range selected at that time by the displayed range selecting section 14 in response to the control command received from the control section 18. The displayed range rotating section 16 rotates the displayed range selected at that time by the displayed range selecting section 14 in an arbitrary direction in response to the control command received from the control section 13.

Figure 2:
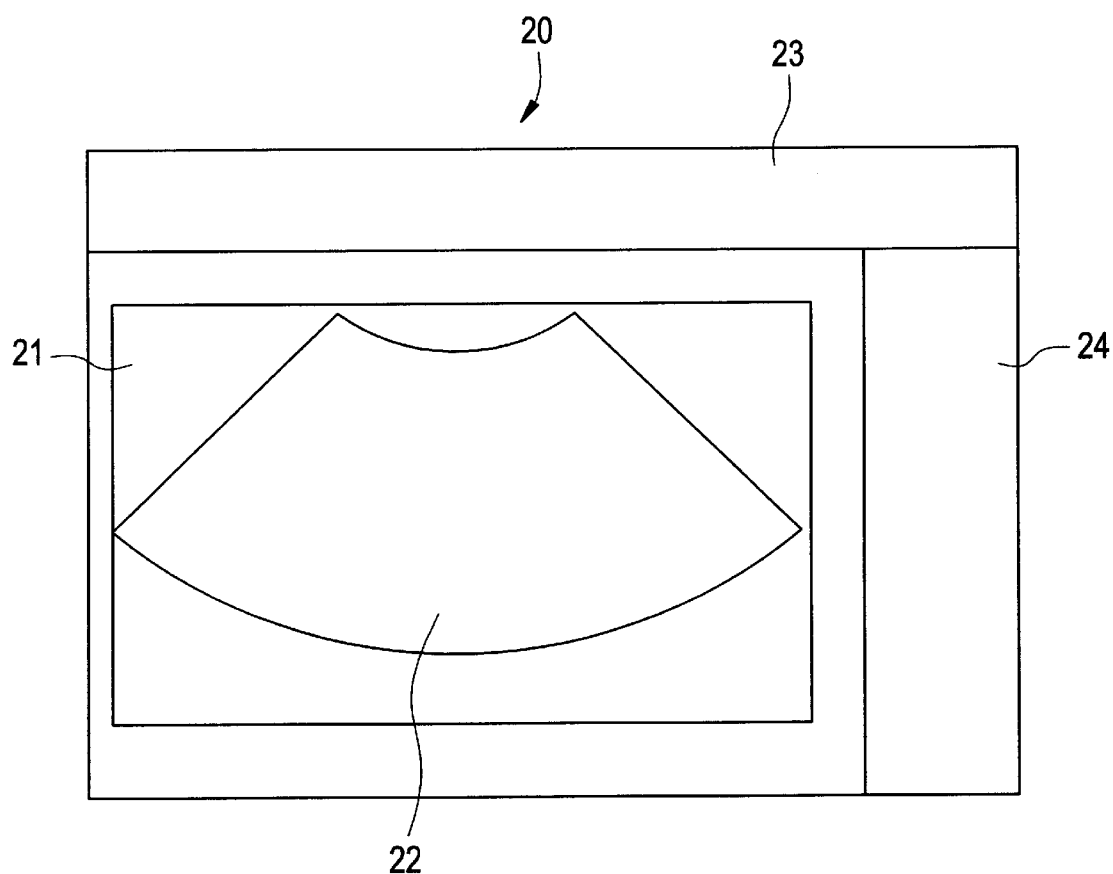
FIG. 2 is an explanatory diagram for explaining a monitor screen when a display area forming section forms a single display area.
Figure 3A:
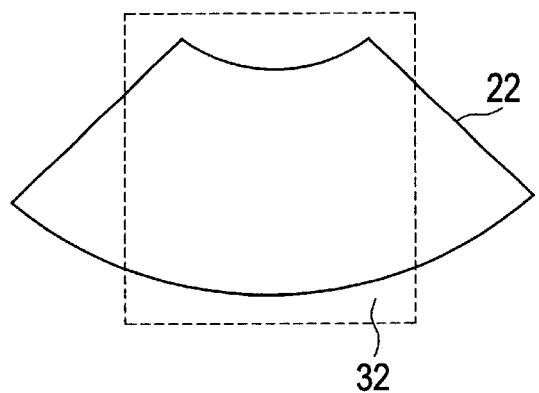
FIG. 3 is an explanatory diagram for explaining a monitor screen when the display area forming section forms two display areas.
Figure 3B:
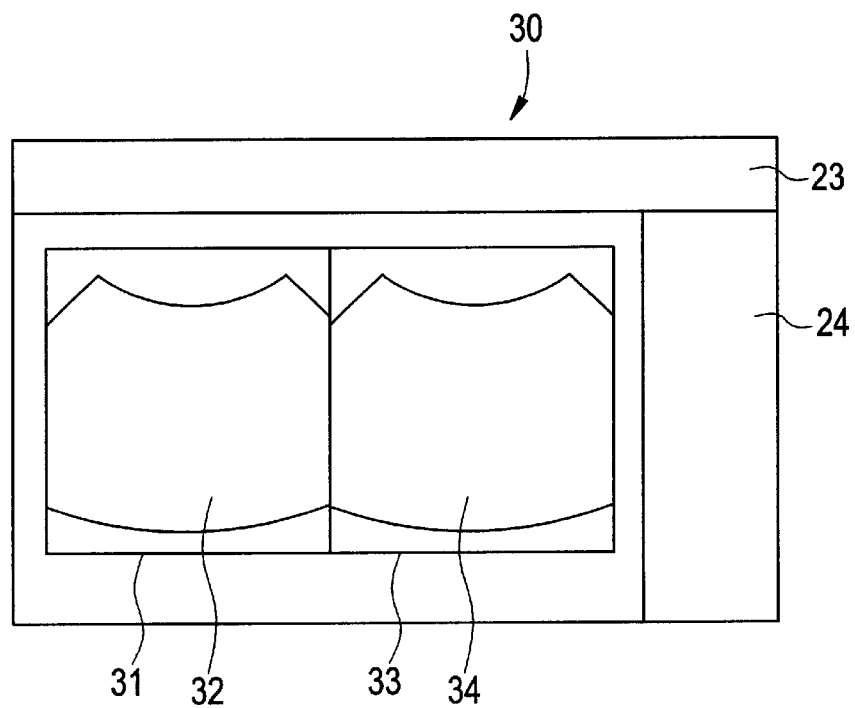

Next, description will be specifically made on a screen displayed on the monitor 2 by the ultrasonic image display apparatus 1 and modification of the display screen using the pointing device 3 with reference to FIGS. 2–13. FIG. 2 is an explanatory diagram for explaining a monitor screen when the display area forming section 17 forms a single display area. FIG. 3 is an explanatory diagram for explaining a monitor screen when the display area forming section 17 forms two display areas. In FIG. 2, the monitor screen 20 comprises a display area 21, an information display area 23, and an operation area 24; and an ultrasonic image 22 is displayed in the display area 21. In FIG. 3(b), the monitor screen 30 comprises display areas 31 and 33, the information display area 23, and the operation area 24; and a displayed range 32 that is part of the ultrasonic image 22 is displayed in the display area 31, and a displayed range 34 of another ultrasonic image is displayed in the display area 33.

The information display area 23 is for displaying information relating to the ultrasonic image and measurement status, and the operation area 24 is for displaying virtual buttons for operations by the pointing device. The information display area 23 and operation area 24 may he in any location and have any size as necessary.

Figure 4A:
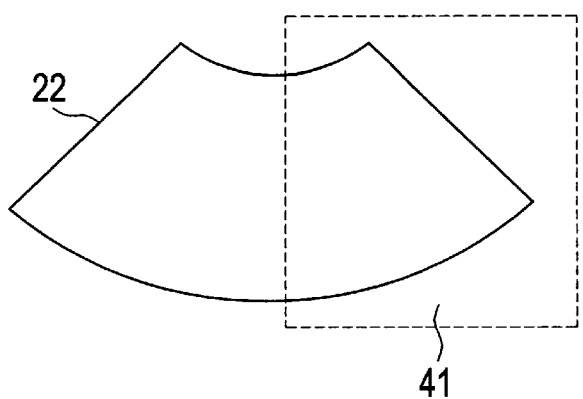
FIG. 4 is an explanatory diagram for explaining a monitor screen in which two display areas are formed and an edge portion of an ultrasonic image is displayed.
Figure 4B:
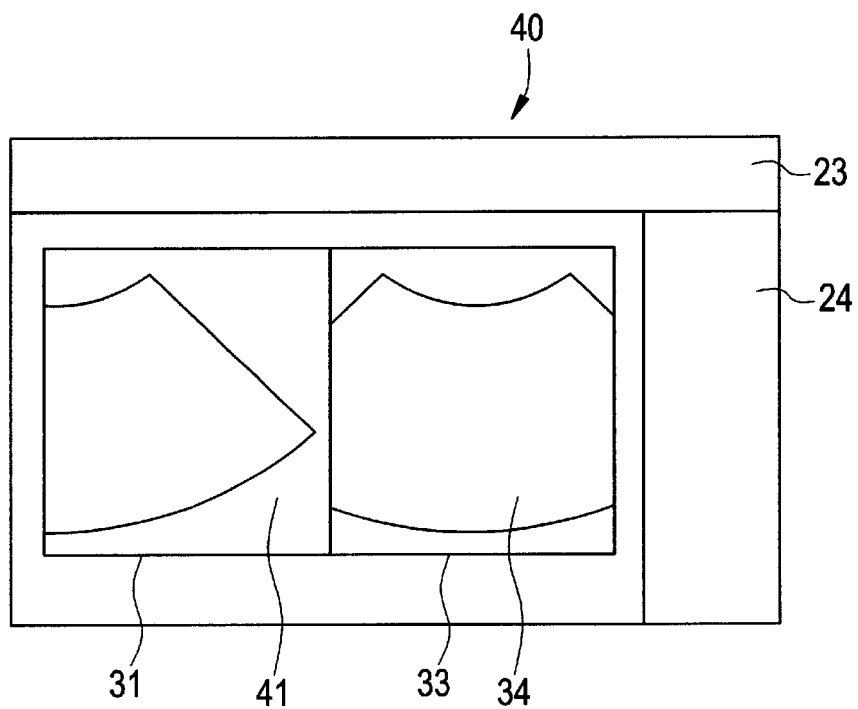

Since the monitor screen 20 forms the single display, a display area 21 of sufficient size can be secured and the whole ultrasonic image 22 can be displayed. On the other hand, since two display areas must be secured in the monitor screen 30, the display areas 31 and 33 are smaller than the display area 21. Accordingly, an ultrasonic image cannot be displayed as a whole in the display area 31 or 33, and a partial region is selectively displayed. As shown in FIG. 3(*a*), in the display area 31, part of the ultrasonic image 22 is selected as the displayed range 32 for display. In FIG. 3(*b*), both in the display areas 32 and 34, portions near the centers of the whole ultrasonic images are selected, and edge portions are not displayed. FIG. 4 is an explanatory diagram for explaining a monitor screen in which two display areas are formed and an edge portion of an ultrasonic image is displayed. In FIG. 4, the monitor screen 40 comprises the display areas 31 and 33, information display area 23 and operation area 24; and a displayed range 41 that is part of the ultrasonic image 22 near an edge portion is displayed in the display area 31, and the displayed range 34 is displayed in the display area 33.

When such a plurality of display areas are formed, an ultrasonic image cannot be displayed as a whole in a display area, and therefore, a need to modify the displayed range of the ultrasonic image in the display area arises. The ultrasonic image display apparatus 1 modifies the displayed range using the movement instruction inputting section 18*a* or position specifying section 18*b* in response to an input from the pointing device 3.

Figure 5A:
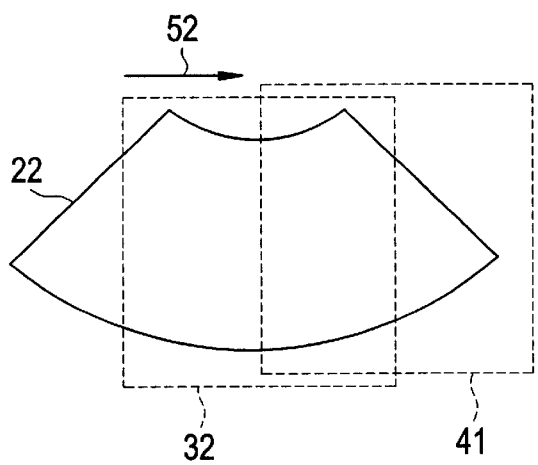
FIG. 5 is an explanatory diagram for explaining an operation for modifying a display area using a movement instruction inputting section.
Figure 5B:
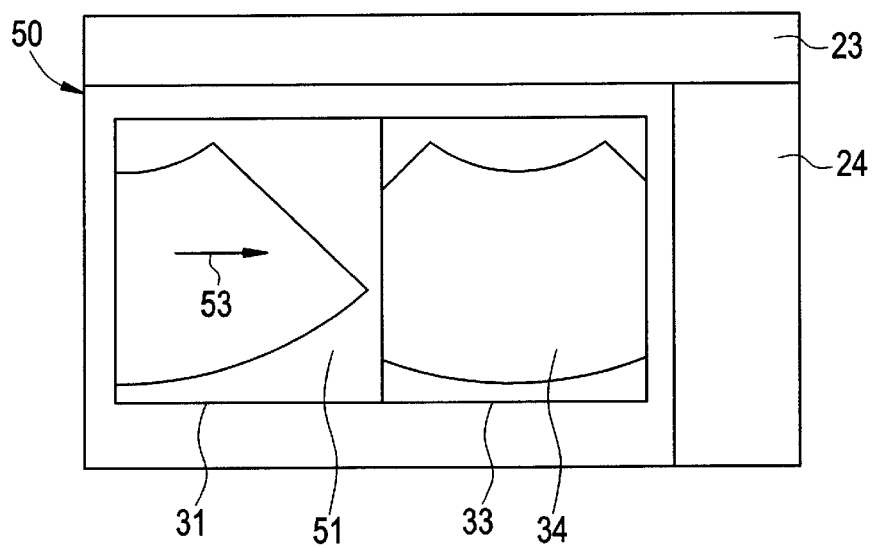
Figure 5C:
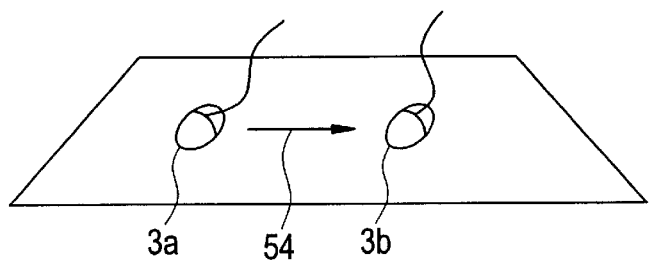

FIG. 5 is an explanatory diagram for explaining an operation for modifying the display area using the movement instruction inputting section 18*a*. When the pointing device 3 is operated and moved, the movement instruction inputting section 18*a* outputs the direction and amount of the movement to the displayed range moving section 15 as a direction and amount of movement of the displayed range of the ultrasonic image 22. Thus, when the pointing device 3 is moved from a position 3*a* to a position 3*b* (FIG. 5(*c*)), the displayed range of the ultrasonic image 22 is moved from the displayed range 32 to the displayed range 41 (FIG. 5(*a*)) corresponding to the amount of pointing device movement 54. The amount of displayed range movement 52 in this case is determined by the amount of the pointing device movement 54. During the operation of the pointing device 3, a monitor screen 50 sequentially changes and displays a displayed range 51 corresponding to the operation of the pointing device 3, as shown in FIG. 5(*b*). That is, the displayed range 51 in the display area 31 scrolls in the direction of movement 53. It should be noted that the operation of the pointing device used for the movement of the displayed range and the operation of the pointing device used for specifying a position on the screen must be discriminated. For example, if a mouse is employed as the pointing device, a movement operation of the mouse with a predetermined button on the mouse pressed, i.e., an operation generally referred to as dragging, causes the movement of the displayed range; and a movement operation of the mouse without pressing any button causes the position specification on the screen, whereby the movement of the displayed range and the position specification on the screen can be discriminated.

Since the direction and amount of movement of the display area can be directly input by an operation of the pointing device 3 by the aforementioned operation for modifying the display area using the movement instruction inputting section 18*a*, the display area can be modified by a simple operation and a desired range of the ultrasonic image 22 can be displayed. While the description has been made on a case in which the displayed range is modified in the display area 31 that is one of two display areas 31 and 33, the displayed range can be modified in the other display range 33 by a similar operation. Which of the plurality of display areas is affected by an operation of the pointing device 3 is determined by a selective action ascribed to the pointing device 3; for example, if a mouse is used as the pointing device 3, the plurality of display areas may be switched from one to another by clicking a predetermined button.

Figure 6A:
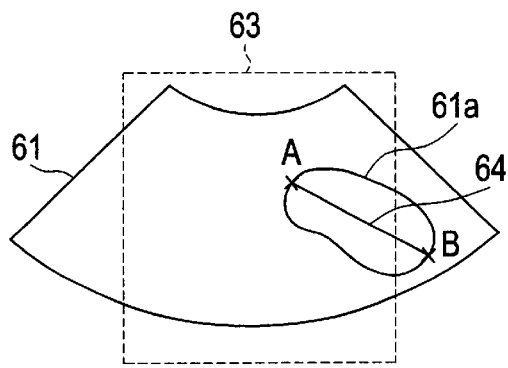
FIG. 6 is an explanatory diagram for explaining an operation for modifying a display area using a position specifying section.
Figure 6B:
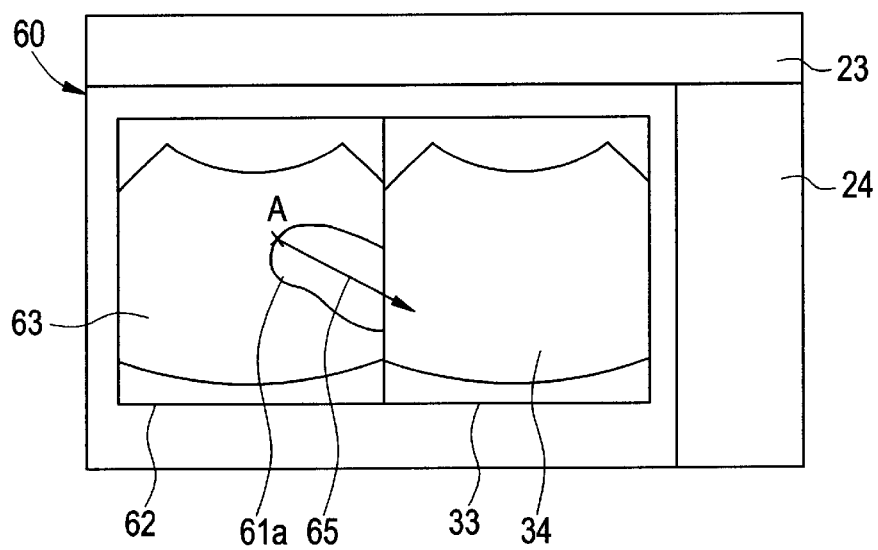
Figure 6C:
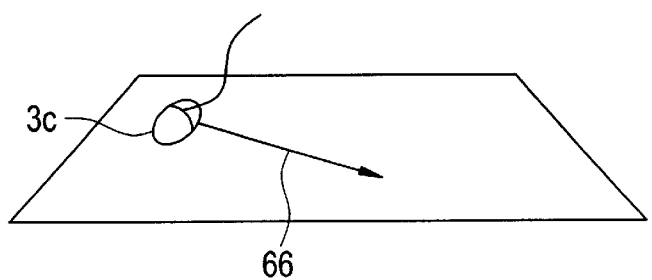

Next, an operation for modifying the display area using the position specifying section 18*b* will be described. FIG. 6 is an explanatory diagram for explaining an operation for modifying the display area using the position specifying section 18*b*. The description hereinbelow will be made on a case in which a subject image 61*a* is present inside an ultrasonic image 61 and the length of the subject image 61*a* is to be measured. FIG. 6(*a*) shows the ultrasonic image 61, which is the whole ultrasonic image; and FIG. 6(*b*) shows a monitor screen 60. The ultrasonic image 61 contains the subject image 61*a* from the center to a portion near an edge of the ultrasonic image 61. The monitor screen 60 comprises display areas 62 and 33, the information display area 23, and the operation area 24; and a displayed range 63 is displayed in the display area 62, and the displayed range 34 is displayed in the display area 33. The displayed range 63 represents a portion near the center of the ultrasonic image 61, and the subject image 61*a* is partially displayed.

When the length of the subject image 61*a*, i.e., a distance 64 between two points A and B shown in FIG. 6(*a*), is to be measured, the pointing device 3 is first operated in the condition of FIG. 6(*b*), and the measurement start point A is specified and selected by the position specifying section 18*b*. Then, the pointing device 3 is moved from a position 3*c* corresponding to the measurement start point A to move the specified position in the display area 62, as shown in FIG. 6(*c*). The amount of the specified position movement 65 on the monitor screen corresponds to the amount of the pointing device movement 66.

Figure 7A:
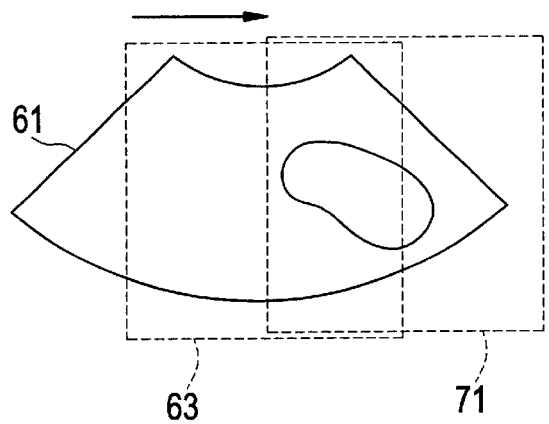
FIG. 7 is an explanatory diagram for explaining an example of modification of a displayed range.
Figure 7B:
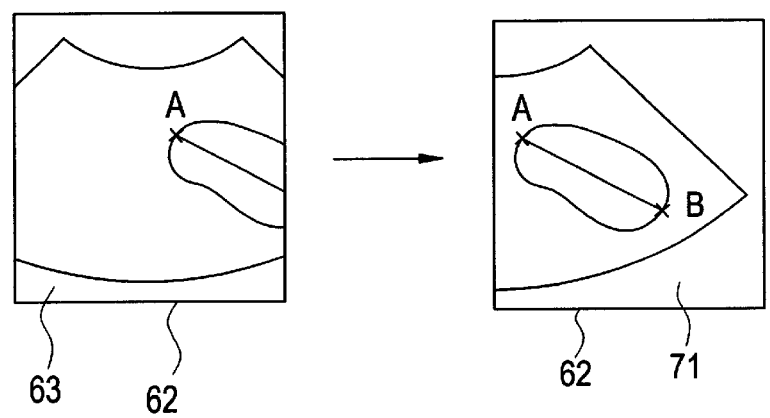
Figure 7C:
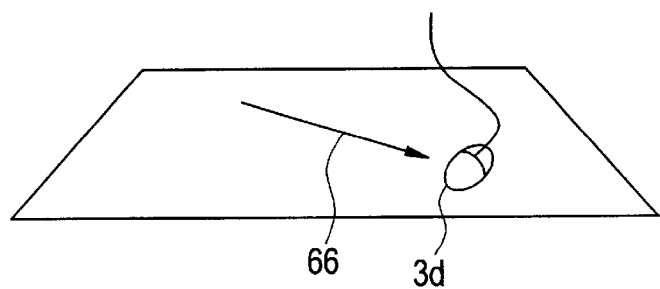

If the specified position is moved outside the display area 62 by the operation of the pointing device 3, the position specifying section 18*b* outputs a command to modify the displayed range to the displayed range moving section 15. The modification of the displayed range is achieved by scrolling the displayed range so that the destination of the movement of the specified position falls within the display area 62. FIG. 7 is an explanatory diagram for explaining an example of the modification of the displayed range. As shown in FIG. 7(*c*), when the pointing device 3 has been moved to a position 3*d* corresponding to the measurement end point B by the amount of pointing device movement 66, the displayed range of the ultrasonic image 61 moves from the displayed range 63 to a displayed range 71 as shown in FIG. 7(*a*). Thus, the displayed range displayed in the display area 62 is scrolled from the displayed range 63 to the displayed range 71 as shown in FIG. 7(*b*), and the measurement end point B is displayed in the display area 62.

When the specified position is thus moved from the inside to the outside of the display area by the operation of the pointing device 3, the displayed range of the ultrasonic image is scrolled so that the destination of the movement falls within the display area, whereby a desired range of the ultrasonic image can be displayed without switching display from multiple display to single display. Moreover, the movement of the displayed range using the position specifying section 18*b* can achieve specification of the distance to be measured and scrolling of the displayed range at the same time; and therefore, the need to switch the display mode in order to display the whole site to be measured is eliminated, and measurement may be started even if only part of the site to be measured is displayed.

Figure 8:
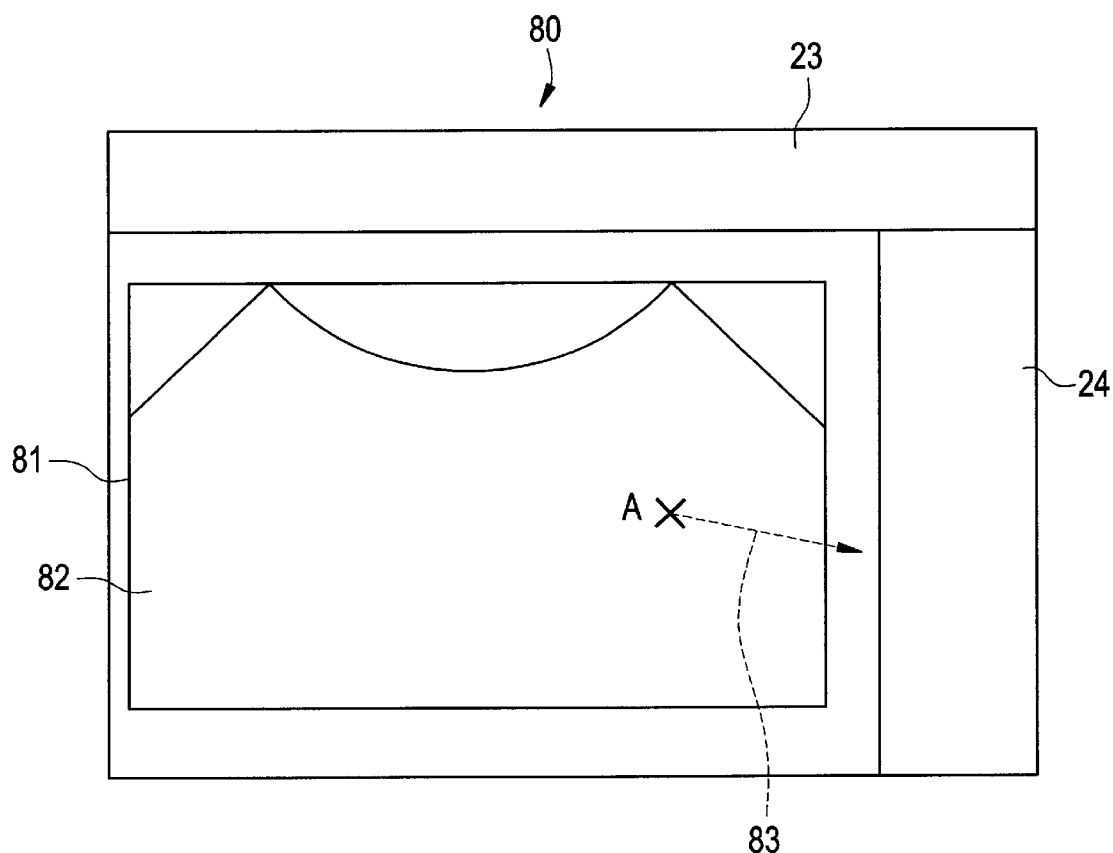
FIG. 8 is an explanatory diagram for explaining a scroll operation by a pointing device in single display.
Figure 9:
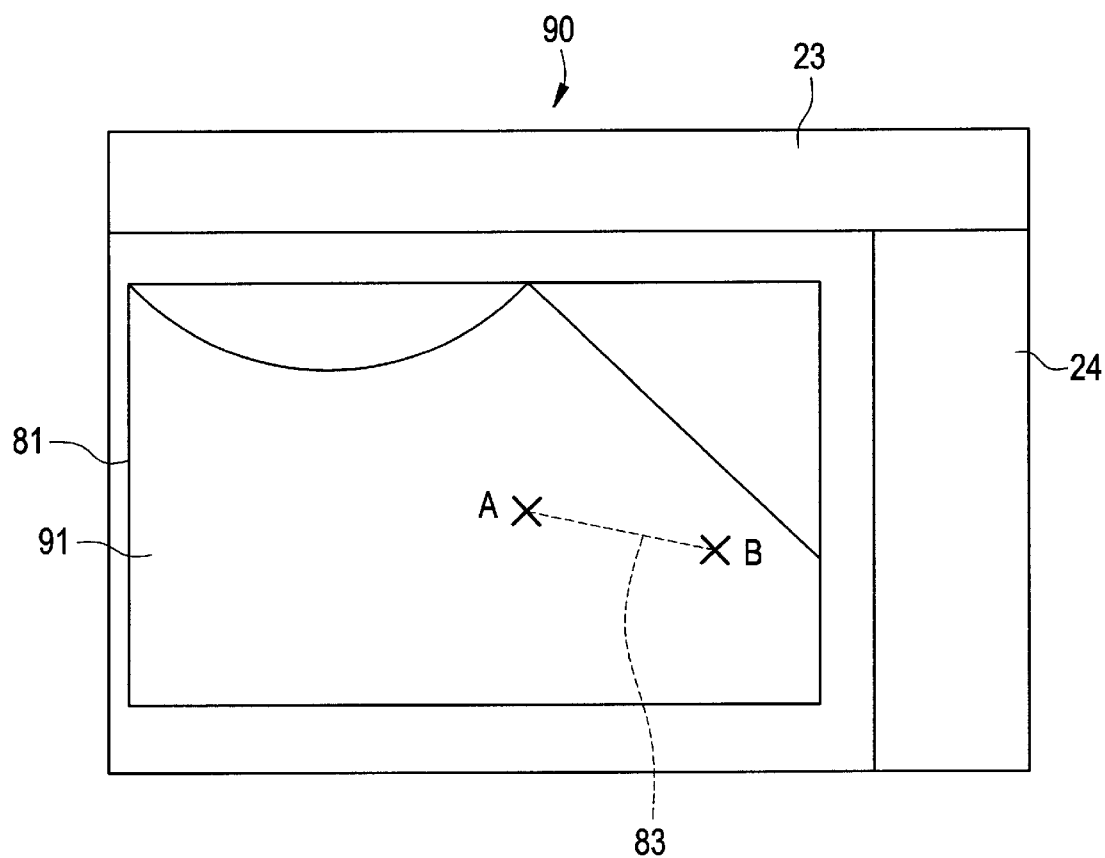
FIG. 9 is an explanatory diagram for explaining a monitor screen in single display after switching a displayed range by an operation of a pointing device.

Such scrolling of the displayed range may be used not only in the multiple display but in the single display. FIG. 8 is an explanatory diagram for explaining a scroll operation by the pointing device in the single display; and FIG. 9 is an explanatory diagram for explaining a monitor screen in the single display after switching the displayed range by an operation of the pointing device. In FIG. 8, a monitor screen 80 comprises a display area 81, the information display area 23, and the operation area 24; and a displayed range 82 of the ultrasonic image with its central portion enlarged is displayed in the display area 81. In the monitor screen 80, for example, when a specified position specified by the pointing device 3 is moved from a specified position A within the display area 81 to a position outside thereof, as indicated by the amount of specified position movement 83, the position specifying section 18b outputs a command to the displayed range moving section 15 to move the displayed range so that the destination of the movement of the specified position falls within the display area 81. The displayed range moving section 15 scrolls and moves the displayed range selected by the displayed range selecting section 14 in response to the command. After scrolling the displayed range, the monitor 2 displays a monitor screen 90 shown in FIG. 9.

The monitor screen 90 comprises the display area 81, information display area 23, and operation area 24; and a displayed range 91 near the edge of the ultrasonic image is displayed in the display area 81. The displayed range 91 represents an image after scrolling the displayed range 82 of the ultrasonic image. The specified position A is identical to that in the displayed range 82 of the ultrasonic image; and a specified position 3 that is the destination of the movement is further displayed. Thus, even if the ultrasonic image is enlarged and displayed in a single display area and part of the ultrasonic image is not displayed, when the specified position is moved from the inside to the outside of the display area by the pointing device 3, the selected range of the ultrasonic image is scrolled so that the destination falls within the display area, whereby a desired range of the ultrasonic image can be displayed. While the description has been made on scrolling of the displayed range by the position specifying section 18b, the displayed range may be moved by using the movement instruction inputting section 18a.

Figure 10:
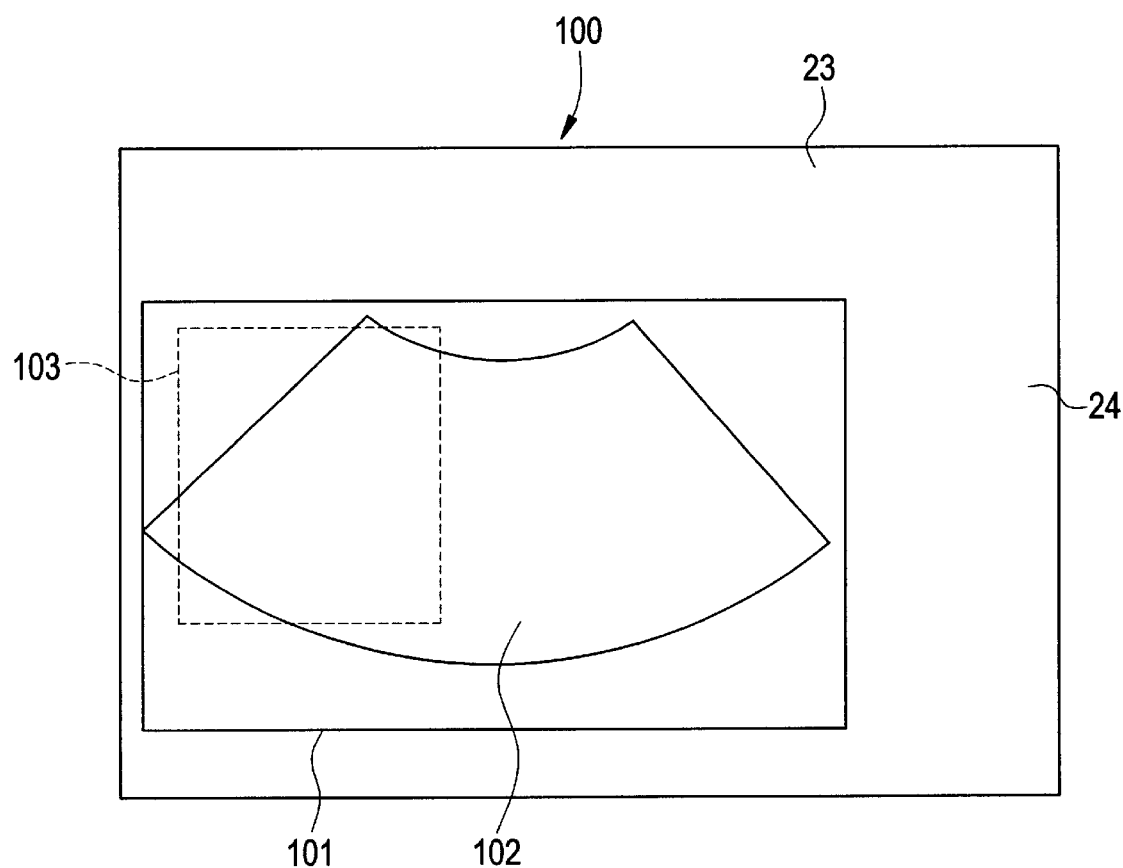
FIG. 10 is an explanatory diagram for explaining a monitor screen in the single display condition before switching to multiple display.
Figure 11:
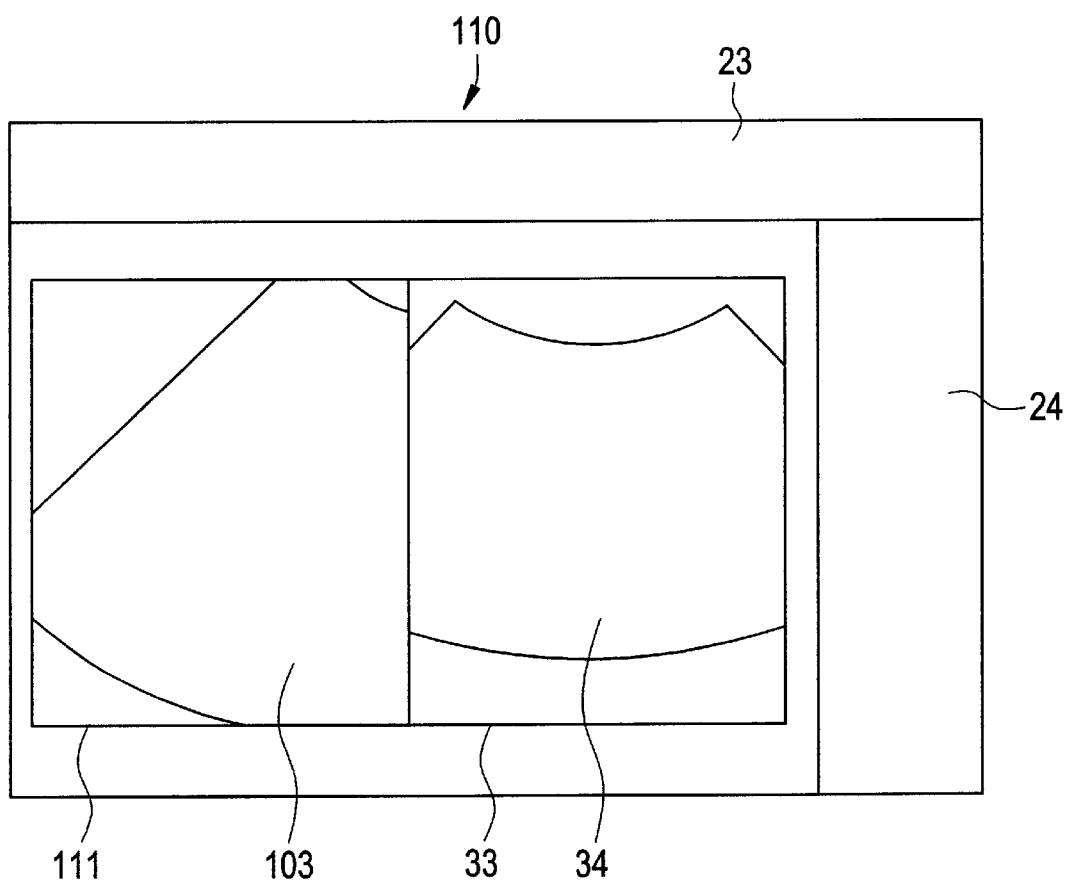
FIG. 11 is an explanatory diagram for explaining a monitor screen after switching from single display to multiple display.

Next, switching from the single display to the multiple display will be described. FIG. 10 is an explanatory diagram for explaining a monitor screen in the single display condition before switching to the multiple display; and FIG. 11 is an explanatory diagram for explaining a monitor screen after switching from the single display to the multiple display. In FIG. 10, a monitor screen 100 comprises a display area 101, the information display area 23, and the operation area 24; and an ultrasonic image 102 is displayed in the display area 101. Here, the ultrasonic image 102 is displayed as a whole. When a desired range of the ultrasonic image 102 is selected as a specified range 103 by the pointing device 3, the display area forming section 14 switches the display from the single display to the multiple display, and the displayed range selecting section 14 displays the specified range 103 in one of the plurality of display areas. At that time, the display area selecting section 14 displays the selected range of the ultrasonic image enlarged as necessary. So that, when the specified range 103 is selected in the single display, it can be specified which is to be executed between enlarged single display in which the specified range 103 is enlarged and displayed in a single display screen and multiple display in which the specified range 103 is displayed in one of the plurality of display areas, it is possible, for example, to display a menu on the screen when the specified range 103 is selected to thereby allow selection of the desired display mode from the menu.

Thus, after switching from the single display to the multiple display, the monitor 2 displays a monitor screen 110 shown in FIG. 11. The monitor screen 110 comprises display areas 111 and 33, the information display area 23, and the operation area 24; and the specified range 103 that is a portion near the edge of the ultrasonic image 102 is displayed enlarged in the display area 111. The ultrasonic image displayed in the display area 111 may be a scan image produced by the image producing section 12, or an ultrasonic image may be arbitrarily selected from the image database 15 and displayed. Thus, when the display is switched from the single display to the multiple display, a desired range is selected from the ultrasonic image displayed in the single display and the range is displayed in one of the plurality of the display areas, whereby a desired display condition can be directly achieved from the single display.

Next, rotation of the displayed range will be described. If the plurality of display areas are displayed at the same time, a plurality of ultrasonic images can be compared; but, to achieve the comparison more easily, it is desirable that the ultrasonic images be displayed at an arbitrary inclination. For example, when ultrasonic images of the right and left kidneys are to be compared, an ultrasonic image of one kidney is stored beforehand, and an ultrasonic image obtained by scanning the other kidney is compared with the stored ultrasonic image. However, since the ultrasonic probe 3 receives an echo signal based on the positional relationship with a subject to be examined and the ultrasonic image is produced based on the echo signal, the two ultrasonic images are not always acquired in the same direction. Accordingly, the location at which the ultrasonic probe is abutted is appropriately adjusted to acquire an image similar to the previously acquired ultrasonic image. The work for such a cumbersome operation can be reduced by an arbitrarily rotatable ultrasonic image.

Figure 12A:
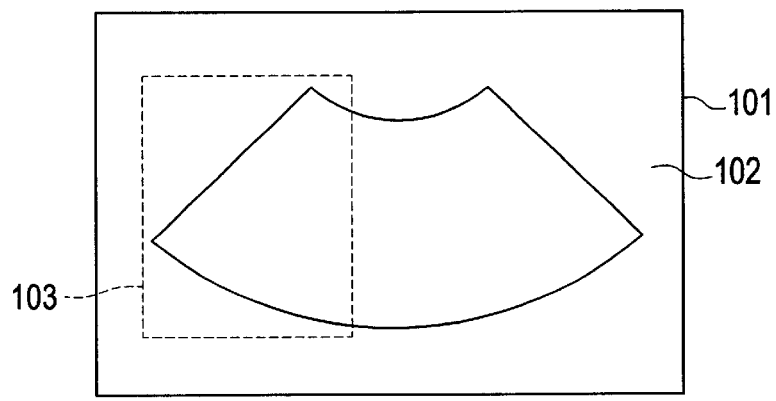
FIG. 12 is an explanatory diagram for explaining an operation for rotating a displayed range of an ultrasonic image.
Figure 12B:
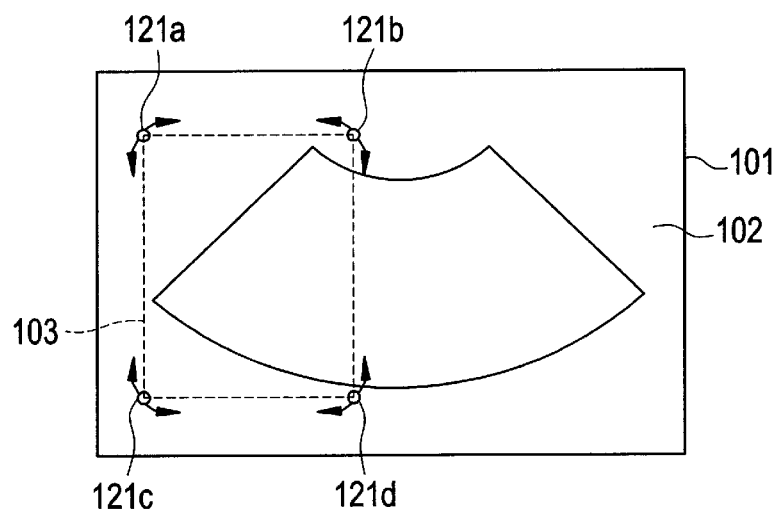
Figure 12C:
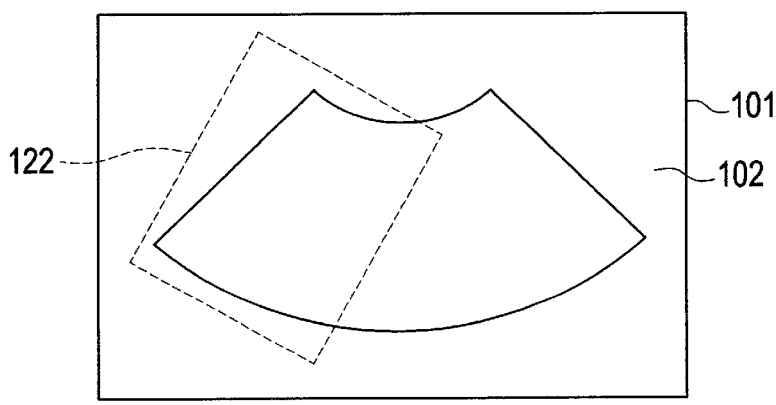

FIG. 12 is an explanatory diagram for explaining an operation for rotating an ultrasonic image. In FIG. 12(a), a display area 101 displays an ultrasonic image 102. When a specified range 103 is selected in the ultrasonic image 102, rotation markers 121a, 121b, 121c and 121d indicating that the specified range is rotatable in the ultrasonic image 102 are displayed, as shown in FIG. 12(b). The user then selects one of the rotation markers 121a, 121b, 121c and 121d by operating the pointing device 3, and specifies an amount of rotation by moving the pointing device 3. The control section 18 transmits the amount of rotation specified by the operation of the pointing device 3 to the displayed range rotating section 16. The displayed range rotating section 16 rotates the specified range based on the received amount of rotation, and then displays a specified range 122 on the monitor 2 as shown in FIG. 12(c). A specific operation for this is as follows, for example: a mouse is employed as the pointing device 3, the position is adjusted to the rotation marker 121a, and a predetermined button on the mouse is pressed to select the rotation marker 121a. Then, the mouse is moved with the button pressed (the mouse is dragged) to rotate the specified range 103 as the rotation marker 121a follows the movement of the mouse.

Figure 13:
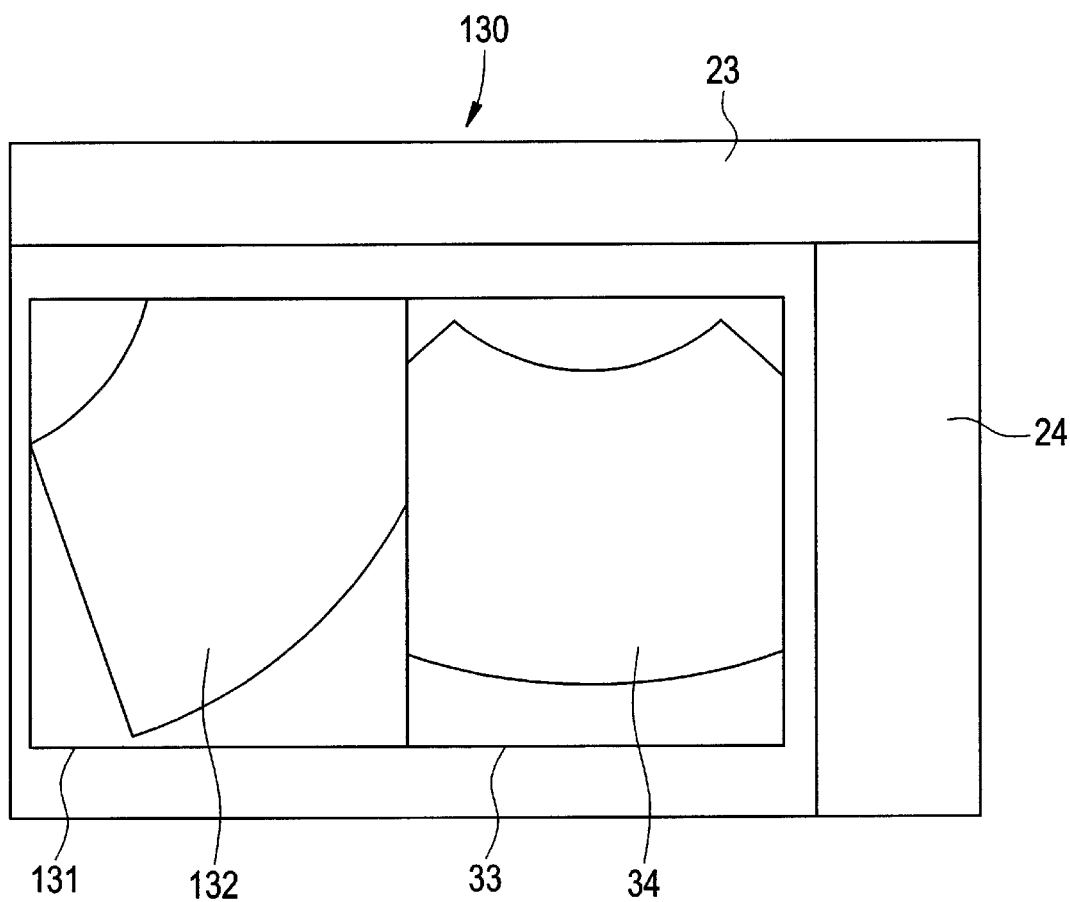
FIG. 13 is an explanatory diagram for explaining a condition of an ultrasonic image displayed after rotation.

After the user has specified a desired amount of rotation, the display area forming section 17 switches the screen display from the single display to the multiple display, and displays the specified range after the rotation in one of the plurality of display areas. FIG. 13 is an explanatory diagram for explaining the ultrasonic image displayed after the rotation. In FIG. 13, a monitor screen 130 comprises display areas 131 and 33, the information display area 23, and the operation area 24; and a displayed range 132 is displayed in the display area 131 and the ultrasonic image 34 is displayed in the display area 33. The displayed range 132 is identical to the specified range 122 determined in FIG. 12(c), and represents an image obtained by rotating the ultrasonic image to a desired angle. Thus, by rotating the display area using the pointing device, a desired displayed range can be easily displayed at a desired angle.

The rotation of the displayed range can be done arbitrarily on an ultrasonic image(s) being displayed in the single display or multiple display. Moreover, the rotation operation can be added to the switching from the single display to the multiple display. By adding the rotation operation to the switching from the single display to the multiple display, an ultrasonic image of a desired displayed range at a desired angle can be displayed by a single operation.

As described above, in the ultrasonic image display apparatus in accordance with the present embodiment, an ultrasonic image based on an echo signal received by the ultrasonic probe 3 is produced by the image producing section 12, a display area is formed on the screen by the display area forming section 17, a displayed range of the ultrasonic image to be displayed in the display area is selected by the displayed range selecting section 14, and scrolling of a selected range and rotation of the displayed range are achieved by the displayed range moving section 15 and displayed range rotating section 16, respectively, based on a position on the monitor screen specified by the pointing device 3; and therefore, a portion displayed on the monitor can be scrolled and rotated to allow use of the whole ultrasonic image in a limited display area, thus improving monitor display condition operating ease.

Although the preceding description of the embodiment has been made on a case in which two display areas are formed as an example of the multiple display and movement and rotation of the displayed range are performed on one of the two display areas, the number of display areas in the multiple display is not limited to two but any number may be used, and the movement and rotation operations on the displayed range may be performed on any one of the number of the display areas.

Moreover, while the description has been made on a case in which the mouse is employed as the pointing device 3 in the embodiment, any input device capable of inputting a position on the monitor screen, such as a trackball or cursor key, may be used.

What is claimed is:

1. An ultrasonic image display apparatus for producing an ultrasonic image based on an echo signal received by an ultrasonic probe and displaying said ultrasonic image on a monitor, said apparatus comprising:

display area forming means for forming on a screen of said monitor a display area;

displayed range selecting means for selecting a first displayed range to be displayed in said display area from said ultrasonic image;

displayed range moving means for conducting movement of said first displayed range of said ultrasonic image;

movement instruction inputting means for inputting a direction and an amount of movement of said first displayed range to said displayed range moving means; and a position specifying means configured to be moved from a first position within said display area to a second position outside said display area, wherein when said position specifying means is moved from the first position within said display area to the second position outside said display area, a second displayed range from said ultrasonic image is displayed in said display area, and said second displayed range includes image data not included within the first displayed range.

2. The ultrasonic image display apparatus of claim 1, wherein said position specifying means specifies an arbitrary position on said monitor screen, and when the position specified by said position specifying means is moved from within said display area to the outside of said display area, said displayed range moving means conducts movement of said first displayed range according to the amount of said movement.

3. The ultrasonic image display apparatus of claim 1, further comprising a single user interface that operates as said movement instruction inputting means or said position specifying means by switching its operation.

4. The ultrasonic image display apparatus of claim 1, wherein said display area forming means is capable of switching display between single display in which a single display area is formed on said monitor screen and multiple display in which a plurality of display areas are formed on said monitor screen.

5. The ultrasonic image display apparatus of claim 1, wherein said ultrasonic image display apparatus further comprises image storing means for storing an ultrasonic image converted from said echo signal as still image data, and said displayed range selecting means selects an ultrasonic image to be displayed and its displayed range from among said ultrasonic image converted from said echo signal and ultrasonic images stored in said image storing means.

6. The ultrasonic image display apparatus of claim 1, wherein when said display area forming means forms a plurality of display areas, said displayed range selecting means selects ultrasonic images to be displayed and their displayed ranges respectively for said plurality of display areas.

7. The ultrasonic image display apparatus of claim 4, wherein when said display area forming means switches display from the single display to the multiple display, said displayed range selecting means selects part of the ultrasonic image displayed in the single display as said first displayed range, and displays said first displayed range in at least one of said plurality of display areas.

8. The ultrasonic image display apparatus of claim 1, further comprising displayed range rotating means for rotating said first displayed range of said ultrasonic image.

9. An ultrasonic image display method for producing an ultrasonic image based on an echo signal received by an ultrasonic probe and displaying said ultrasonic image on a monitor, said method comprising the steps of:

forming on a screen of said monitor a display area in which at least part of said ultrasonic image is displayed;

selecting a first displayed range to be displayed in said display area from said ultrasonic image;

conducting movement of said first displayed range of said ultrasonic image;

inputting a direction and an amount of the movement of said first displayed range to a displayed range moving means;

moving from a first position within said display area to a second position outside said display area; and displaying, from said ultrasonic image, a second displayed range within said display area when said moving from a first position within said display area to a second position outside said display area occurs, wherein said second displayed range includes image data not included within said first displayed range.

10. The ultrasonic image display method of claim 9, wherein said ultrasonic image display method further comprises a position specifying step of specifying an arbitrary position on said monitor screen, and when the position specified by said position specifying step is moved from within said display area to the outside of said display area, said conducting movement step conducts movement of said first displayed range according to the amount of said movement.

11. The ultrasonic image display method of claim 9, wherein said conducting movement step and said inputting a direction step are executed by a single user interface.

12. The ultrasonic image display method of claim 9, wherein said forming on a screen step is capable of switching display between single display in which a single display area is formed on said monitor screen and multiple display in which a plurality of display areas are formed on said monitor screen.

13. The ultrasonic image display method of claim 12, wherein when said forming on a screen step switches display from the single display to the multiple display, said selecting a first displayed range step selects part of the ultrasonic image displayed in the single display as said first displayed range, and displays said first displayed range in at least one of said plurality of display areas.

14. The ultrasonic image display method of claim 9, wherein said ultrasonic image display method further comprises an image storing step of storing an ultrasonic image converted from said echo signal as still image data, and said selecting a first displayed range step selects an ultrasonic image to be displayed and said first displayed range from among said ultrasonic image converted from said echo a ultrasonic images stored by said image storing step.

15. The ultrasonic image display method of claim 9, wherein said forming on a screen step forms a plurality of display areas, said selecting a first displayed range step selects ultrasonic images to be displayed and their displayed ranges respectively for said plurality of display areas.

16. The ultrasonic image display method of claim 9, further comprising a displayed range rotating step of rotating said first displayed range of said ultrasonic image.

17. An ultrasonic image display apparatus for producing an ultrasonic image based on an echo signal received by an ultrasonic probe and displaying the ultrasonic image on a monitor, said apparatus comprising:

a display area forming section configured to form on a screen of said monitor a display area;

a displayed range selecting section configured to enable a selection of a first displayed range to be displayed in said display area from the ultrasonic image;

a displayed range moving section configured to enable a movement of the first displayed range of the ultrasonic image;

a movement instruction inputting section configured to enable inputting a direction and an amount of movement of the first displayed range; and a position specifying section configured to be moved from a first position within said display area to a second position outside said display area, wherein when said position specifying section is moved from the first position within said display area to the second position outside said display area, a second displayed range from said ultrasonic image is displayed in said display area, and said second displayed range includes image data not included within the first displayed range.

18. The ultrasonic image display apparatus of claim 17, wherein said position specifying section is further configured to enable specifying an arbitrary position on said monitor screen, and when the position specified by said position specifying section is moved from within said display area to the outside of said display area, said displayed range moving means conducts movement of the first displayed range according to the amount of the movement.

19. The ultrasonic image display apparatus of claim 17, wherein said display area forming section is further configured to enable switching between a single display in which a single display area is formed on said monitor screen and a multiple display in which a plurality of display areas are formed on said monitor screen.

20. The ultrasonic image display apparatus of claim 17, further comprising a displayed range rotating section for rotating the first displayed range of the ultrasonic image.

* * * * *

UNITED STATES PATENT AND TRADEMARK OFFICE
CERTIFICATE OF CORRECTION

PATENT NO.    : 6,743,176 B2
DATED         : June 1, 2004
INVENTOR(S)   : Sei Kato It is certified that error appears in the above-identified patent and that said Letters Patent is hereby corrected as shown below:

Column 15,
Line 36, after "echo" delete "a" and insert -- signal and --.

Signed and Sealed this

Second Day of May, 2006

JON W. DUDAS
*Director of the United States Patent and Trademark Office*